(12) United States Patent
Urabe et al.

(10) Patent No.: US 11,844,656 B2
(45) Date of Patent: Dec. 19, 2023

(54) ULTRASOUND DIAGNOSTIC APPARATUS, METHOD OF CONTROLLING ULTRASOUND DIAGNOSTIC APPARATUS, AND NON-TRANSITORY COMPUTER-READABLE RECORDING MEDIUM STORING THEREIN COMPUTER-READABLE PROGRAM FOR CONTROLLING ULTRASOUND DIAGNOSTIC APPARATUS

(71) Applicant: Konica Minolta, Inc., Tokyo (JP)

(72) Inventors: Makiko Urabe, Kanagawa (JP); Yoshihiro Takeda, Tokyo (JP); Akihiro Kawabata, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 136 days.

(21) Appl. No.: 17/126,944

(22) Filed: Dec. 18, 2020

(65) Prior Publication Data
US 2021/0186467 A1    Jun. 24, 2021

(30) Foreign Application Priority Data
Dec. 24, 2019   (JP) ................. 2019-232736

(51) Int. Cl.
*A61B 8/00* (2006.01)
*A61B 8/14* (2006.01)
(Continued)

(52) U.S. Cl.
CPC ............... *A61B 8/54* (2013.01); *A61B 8/06* (2013.01); *A61B 8/0891* (2013.01); *A61B 8/145* (2013.01);
(Continued)

(58) Field of Classification Search
CPC .......... A61B 8/54; A61B 8/06; A61B 8/0891; A61B 8/145; A61B 8/463; A61B 8/469;
(Continued)

(56) References Cited

U.S. PATENT DOCUMENTS 9,668,714 B2 *   6/2017   Call ................... G01S 15/8927
2011/0150274 A1 *  6/2011   Patwardhan ............ G06T 7/149
                                                        382/209
(Continued)

FOREIGN PATENT DOCUMENTS

JP   2001-218768 A   8/2001
JP   2002-052026 A   2/2002
(Continued)

OTHER PUBLICATIONS

Office Action dated Apr. 27, 2023 for corresponding Chinese Patent Application No. 202011515937.4, with English translation.
(Continued)

*Primary Examiner* — Yi-Shan Yang
*Assistant Examiner* — Kaitlyn E Sebastian
(74) *Attorney, Agent, or Firm* — LUCAS & MERCANTI, LLP

(57) ABSTRACT

An ultrasound diagnostic apparatus includes: a hardware processor that search for a blood vessel position of a subject in a tomographic image and automatically setting a region corresponding to the blood vessel position detected in the tomographic image as a measurement region for generating a Doppler image. In a case where a measurement region has been already set or in a case where a specified position specified by a user exists when the hardware processor automatically sets the measurement region, the hardware processor executes processing of searching for the blood vessel position such that the measurement region is auto-
(Continued)

matically set near the measurement region that has been already set or the specified position.

18 Claims, 13 Drawing Sheets

(51) Int. Cl.
*A61B 8/08* (2006.01)
*A61B 8/06* (2006.01)

(52) U.S. Cl.
CPC .............. *A61B 8/463* (2013.01); *A61B 8/469* (2013.01); *A61B 8/488* (2013.01); *A61B 8/5207* (2013.01); *A61B 8/5223* (2013.01)

(58) Field of Classification Search
CPC ..... A61B 8/488; A61B 8/5207; A61B 8/5223; A61B 8/44; A61B 8/4444; A61B 8/467; A61B 8/5215
See application file for complete search history.

(56) References Cited

U.S. PATENT DOCUMENTS

| | | | | |
|---|---|---|---|---|
| 2012/0157850 A1* | 6/2012 | Sumi | ...................... | A61B 8/145 600/443 |
| 2012/0321163 A1* | 12/2012 | Akahori | ................ | G06T 11/006 382/131 |
| 2014/0221838 A1* | 8/2014 | Loupas | ............... | G01S 7/52071 600/454 |

FOREIGN PATENT DOCUMENTS

| | | | | | |
|---|---|---|---|---|---|
| JP | 2012061074 A | * | 3/2012 | ........... | A61B 5/0037 |
| JP | 2014-528266 A | | 10/2014 | | |
| JP | 2014-217745 A | | 11/2014 | | |
| JP | 2019534110 A | * | 11/2017 | | |
| WO | WO-2014115841 A1 | * | 7/2014 | ............. | A61B 6/037 |
| WO | WO-2018094118 A1 | * | 5/2018 | ............... | A61B 8/12 |

OTHER PUBLICATIONS

Notice of Reasons for Rejection dated Jun. 13, 2023 for corresponding Japanese Patent Application No. 2019-232736, with English translation.

Notice of Reasons for Rejection dated Oct. 10, 2023 for corresponding Japanese Patent Application No. 2019-232736, with English translation.

* cited by examiner

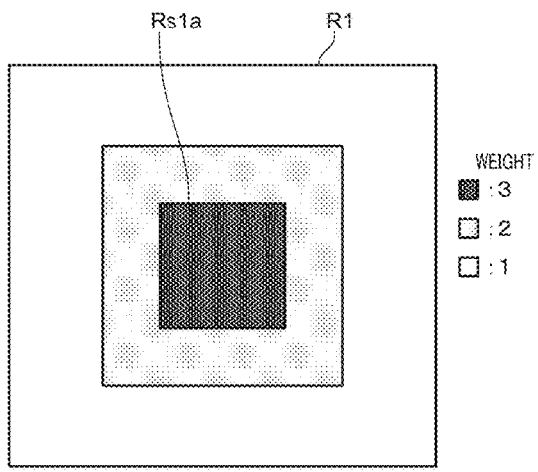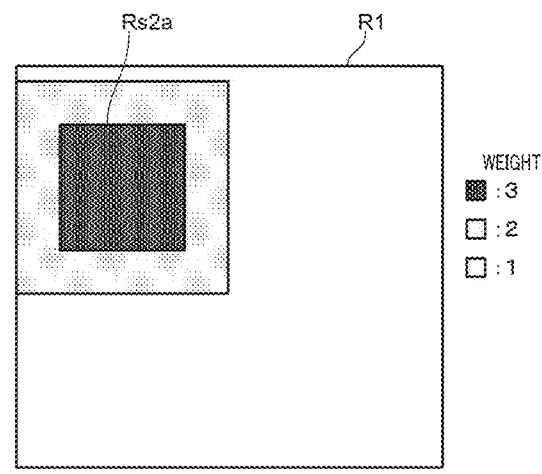
FIG. 5A
FIG. 5B

ULTRASOUND DIAGNOSTIC APPARATUS, METHOD OF CONTROLLING ULTRASOUND DIAGNOSTIC APPARATUS, AND NON-TRANSITORY COMPUTER-READABLE RECORDING MEDIUM STORING THEREIN COMPUTER-READABLE PROGRAM FOR CONTROLLING ULTRASOUND DIAGNOSTIC APPARATUS

CROSS REFERENCE TO RELATED APPLICATIONS

The entire disclosure of Japanese Patent Application No. 2019-232736 filed on Dec. 24, 2019 is incorporated herein by reference in its entirety.

BACKGROUND

Technological Field

The present disclosure relates to an ultrasound diagnostic apparatus, a method of controlling an ultrasound diagnostic apparatus, and a non-transitory computer-readable recording medium storing therein a computer-readable program for controlling an ultrasound diagnostic apparatus.

Description of Related Art

In the related art, an ultrasound diagnostic apparatus that measures a state of blood flow (for example, blood flow velocity, blood flow direction, power, variance of blood flow velocity, and the like) flowing through a blood vessel in a subject by a Doppler shift frequency of an ultrasonic echo when an ultrasound beam is transmitted is known (for example, see Japanese Unexamined Patent Application Publication (Translation of PCT Application) No. 2014-528266).

Note that, in this type of ultrasound diagnostic apparatus, a technique of automatically setting a measurement region based on a tomographic image generated when B mode is executed or based on Doppler signals experimentally detected at each position has been studied in the related art in order to reduce an operation load for a user when setting a measurement region related to a Doppler mode (for example, a color Doppler mode, a power Doppler mode, and a Pulse Width (PW) Doppler mode) for measuring a state of blood flow (for example, see Japanese Unexamined Patent Application Publication (Translation of PCT Application) No. 2014-528266).

In the actual field of ultrasonography, however, a user wants to perform ultrasonography, while viewing a tomographic image displayed on a monitor, by setting a portion of a blood vessel projected in the tomographic image, for which the user wishes to examine a state of blood flow, as a measurement region. Accordingly, an automatically set measurement region cannot be necessarily said to meet the user's intention.

Further, since the user performs ultrasonography while switching an imaging mode executed in the ultrasound diagnostic apparatus described above among the B mode, the color Doppler mode, the power Doppler mode, the PW Doppler mode and the like, it is complicated for the user to reset the measurement region every time the mode is changed. Hereinafter, the color Doppler mode, the power Doppler mode and the PW Doppler mode are collectively referred to as "Doppler mode".

SUMMARY

The present disclosure has been made in view of the above-described problems, and an object thereof is to provide an ultrasound diagnostic apparatus, a method of controlling an ultrasound diagnostic apparatus, and a non-transitory computer-readable recording medium storing therein a computer-readable program for controlling an ultrasound diagnostic apparatus, which are capable of reducing an operation load for a user when setting a measurement region in the Doppler mode while reflecting the user's intention.

To achieve at least one of the abovementioned objects, according to an aspect of the present invention, an ultrasound diagnostic apparatus reflecting one aspect of the present invention comprises:

a hardware processor that:

generates a tomographic image of an inside of a subject based on a reception signal related to an ultrasonic echo of a first ultrasound beam transmitted so as to scan the inside of the subject;

searches for a position of a blood vessel of the subject in the tomographic image and automatically sets a region corresponding to the position of the blood vessel detected in the tomographic image as a measurement region; and generates a Doppler image based on a reception signal related to an ultrasonic echo of a second ultrasound beam transmitted to the measurement region, wherein in a case where a measurement region has been already set or in a case where a specified position specified by a user exists when the hardware processor automatically sets the measurement region, the hardware processor executes processing of searching for the position of the blood vessel such that the measurement region is automatically set near the measurement region that has been already set or near the specified position.

To achieve at least one of the abovementioned objects, according to an aspect of the present invention, a method of controlling an ultrasound diagnostic apparatus reflecting one aspect of the present invention comprises:

generating a tomographic image of an inside of a subject based on a reception signal related to an ultrasonic echo of a first ultrasound beam transmitted so as to scan the inside of the subject;

searching for a position of a blood vessel of the subject in the tomographic image, and automatically setting a region corresponding to the position of the blood vessel detected in the tomographic image as a measurement region; and generating a Doppler image based on a reception signal related to an ultrasonic echo of a second ultrasound beam transmitted to the measurement region, wherein in a case where a measurement region has been already set or in a case where a specified position specified by a user exists when the measurement region is automatically set, processing of searching for the position of the blood vessel is executed such that the measurement region is automatically set near the measurement region that has been already set or near the specified position.

To achieve at least one of the abovementioned objects, according to an aspect of the present invention, a non-transitory computer-readable recording medium storing therein a computer-readable program for controlling an ultrasound diagnostic apparatus reflecting one aspect of the present invention, the program causing a computer to perform:

generating a tomographic image of an inside of a subject based on a reception signal related to an ultrasonic echo of a first ultrasound beam transmitted so as to scan the inside of the subject;

searching for a position of a blood vessel of the subject in the tomographic image, and automatically setting a region corresponding to the position of the blood vessel detected in the tomographic image as a measurement region; and generating a Doppler image based on a reception signal related to an ultrasonic echo of a second ultrasound beam transmitted to the measurement region, wherein in a case where a measurement region has been already set or in a case where a specified position specified by a user exists when the measurement region is automatically set, processing of searching for the position of the blood vessel is executed such that the measurement region is automatically set near the measurement region that has been already set or near the specified position.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIGS. 5A and 5B are diagrams illustrating examples of weights set by a measurement region setting section according to the embodiment for each position of a tomographic image as a search condition;

FIG. 12 is a diagram illustrating an example of a timing at which the Doppler parameter setting section according to the embodiment executes processing of automatically setting a measurement region or the like;

FIG. 13 is a diagram illustrating an example of a timing at which the Doppler parameter setting section according to the embodiment executes the processing of automatically setting a measurement region or the like;

FIG. 14 is a diagram illustrating an example of a timing at which the Doppler parameter setting section according to the embodiment executes the processing of automatically setting a measurement region or the like.

DETAILED DESCRIPTION OF EMBODIMENTS

Figure 1:
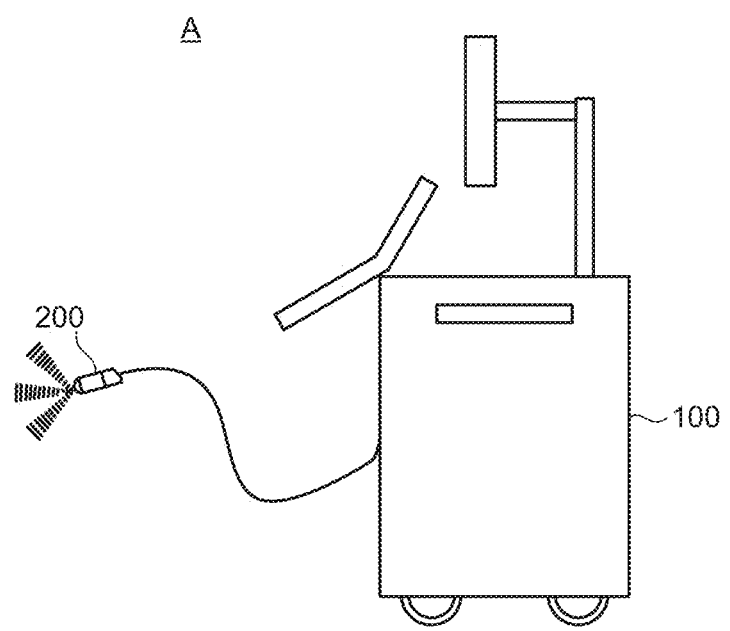
FIG. 1 is a diagram illustrating an external view of an ultrasound diagnostic apparatus according to an embodiment.

Hereinafter, one or more embodiments of the present invention will be described with reference to the drawings. However, the scope of the invention is not limited to the disclosed embodiments.

Hereinafter, preferred embodiments of the present disclosure will be described in detail with reference to the attached drawings. Note that, components having substantially the same functions are assigned the same reference numerals in the description and drawings to omit duplicated descriptions thereof.

[Configuration of Ultrasound Diagnostic Apparatus]

Hereinafter, a configuration of an ultrasound diagnostic apparatus according to an embodiment of the present invention will be described with reference to FIGS. 1, 2 and 3.

Figure 2:
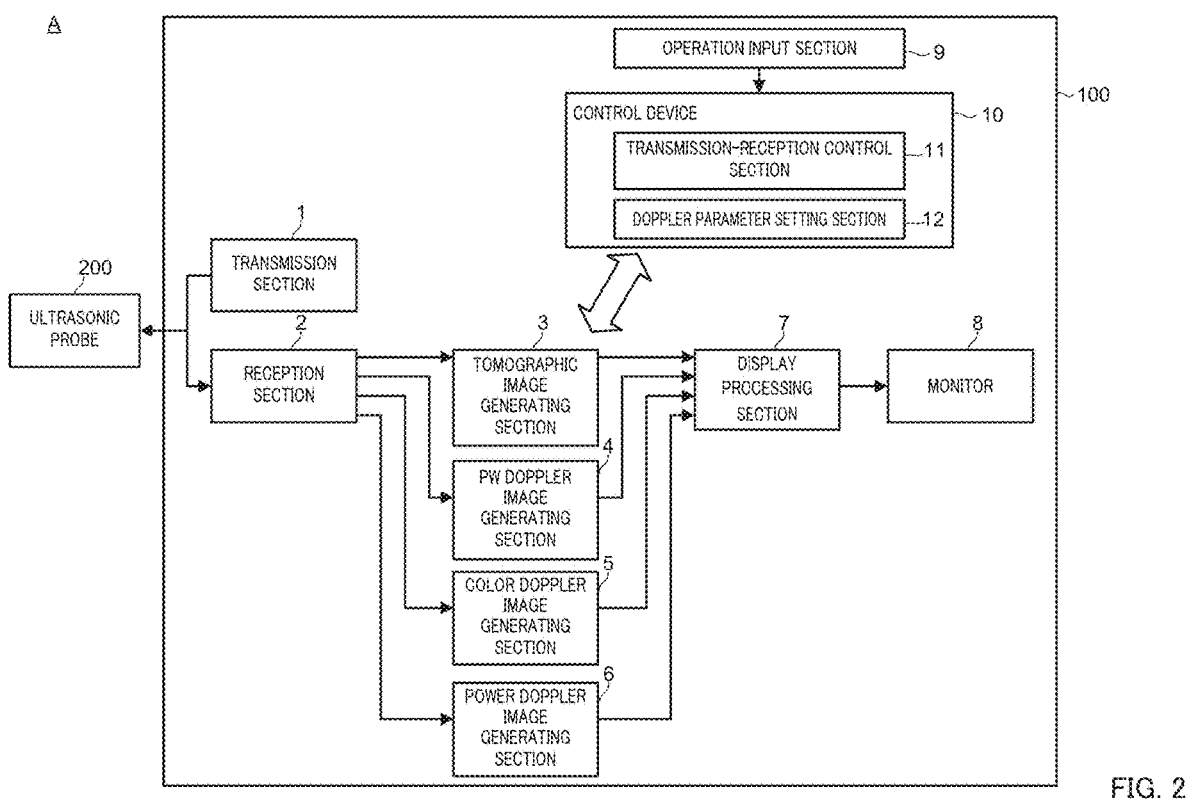
FIG. 2 is a diagram illustrating an overall configuration of the ultrasound diagnostic apparatus according to the embodiment.

FIG. 1 is a diagram illustrating an external view of ultrasound diagnostic apparatus A according to the present embodiment. FIG. 2 is a diagram illustrating an overall configuration of ultrasound diagnostic apparatus A according to the present embodiment.

Figure 3:
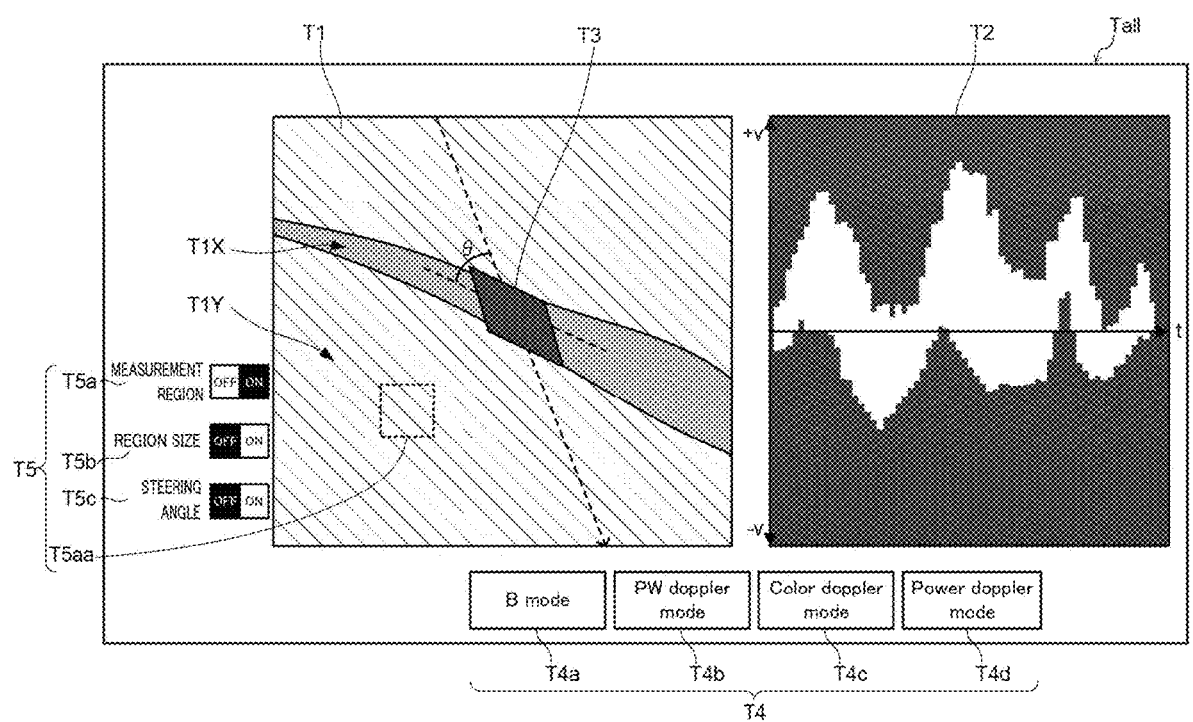
FIG. 3 is a diagram illustrating an example of a monitor screen, which is displayed when a blood flow is measured, in the ultrasound diagnostic apparatus according to the embodiment.

FIG. 3 is a diagram illustrating an example of a monitor screen, which is displayed when a blood flow is measured, in ultrasound diagnostic apparatus A according to the present embodiment.

Ultrasound diagnostic apparatus A is used to visualize the shape, properties, or kinetics of an inside of a subject as an ultrasound image to perform an image diagnosis. Note that, in the present embodiment, a description will be given of a form in which ultrasound diagnostic apparatus A selectively executes one of the B mode, the color Doppler mode, the power Doppler mode, and the Pulse Width (PW) Doppler mode as an imaging mode for ultrasound diagnostic apparatus A to image a subject in accordance with a switching operation of a user.

As illustrated in FIG. 1, ultrasound diagnostic apparatus A includes ultrasound diagnostic apparatus main body 100 and ultrasonic probe 200. Ultrasound diagnostic apparatus main body 100 and ultrasonic probe 200 are connected to each other via a cable.

Ultrasonic probe 200 functions as an acoustic sensor that transmits an ultrasound beam (here, approximately 1 to 30 MHz) into a subject (for example, a human body), receives an ultrasonic echo resulting from part of the transmitted ultrasound beam reflected in the subject, and converts the ultrasonic echo into an electric signal.

A user brings an ultrasound-beam transmission-reception surface of ultrasonic probe 200 into contact with a subject, operates ultrasound diagnostic apparatus A, and performs an ultrasonic diagnosis. Note that, it is assumed here that ultrasonic probe 200 transmits an ultrasound beam from an outer surface of the subject into the subject and receives the resulting ultrasonic echo. However, ultrasonic probe 200 may be an ultrasonic probe that is used by being inserted into e.g. the alimentary canal or a blood vessel, or into the coelom or the like. Further, as ultrasonic probe 200, any probe such as a convex probe, a linear probe, a sector probe, and a 3D probe is applicable.

Ultrasonic probe 200 includes, for example, a plurality of transducers (for example, piezoelectric elements) arranged in a matrix and a channel switching section (for example, a multiplexer) for performing switching control to turn on and off of the driving states of the plurality of transducers individually or for each block (hereinafter referred to as "channel").

Each transducer of ultrasonic probe 200 converts a voltage pulse generated by ultrasound diagnostic apparatus main body 100 (transmission section 1) into an ultrasound beam, transmits the ultrasound beam into a subject, receives an ultrasonic echo reflected in the subject, converts the ultrasonic echo into an electric signal (hereinafter referred to as "reception signal"), and outputs the reception signal to ultrasound diagnostic apparatus main body 100 (reception section 2).

Ultrasound diagnostic apparatus main body 100 includes transmission section 1, reception section 2, tomographic image generating section 3, PW Doppler image generating section 4, color Doppler image generating section 5, power Doppler image generating section 6, display processing section 7, monitor 8, operation input section 9, and control device 10.

Transmission section 1 is a transmitter that sends out a voltage pulse that is a driving signal to ultrasonic probe 200. Transmission section 1 includes, for example, a high-frequency pulse oscillator, a pulse setting section, and the like. Transmission section 1 adjusts a voltage pulse generated by the high-frequency pulse oscillator to a voltage amplitude, a pulse width, and a sending-out timing set by the pulse setting section, and sends out the voltage pulse for each channel of ultrasonic probe 200.

Transmission section 1 includes the pulse setting section for each of a plurality of channels of ultrasonic probe 200 and is configured such that the voltage amplitude, the pulse width, and the sending-out timing of the voltage pulse can be set for each of the plurality of channels. For example, transmission section 1 sets appropriate delay times for the plurality of channels to change a target depth or generate different pulse waveforms (for example, transmission section 1 sends out a single-wave pulse in the B mode and a four-wave pulse of in the PW Doppler mode).

Reception section 2 is a receiver that performs reception processing of a reception signal related to an ultrasonic echo and generated by ultrasonic probe 200. Reception section 2 includes a preamplifier, an AD conversion section, a reception beamformer, and a processing system switching section.

The preamplifier of reception section 2 amplifies a reception signal related to a weak ultrasonic echo for each channel, and the AD conversion section of reception section 2 converts the reception signal into a digital signal. In addition, the reception beamformer of reception section 2 unifies reception signals of the plurality of channels by phasing addition of reception signals of each channel, to thereby generate acoustic line data. Further, the processing system switching section of reception section 2 controls switching of sections to which the reception signal generated by the reception beamformer is transmitted, and outputs the reception signal to one of tomographic image generating section 3, PW Doppler image generating section 4, color Doppler image generating section 5, and power Doppler image generating section 6 in accordance with the operation mode to be executed.

Tomographic image generating section 3 acquires a reception signal from reception section 2 when the B mode is executed, and generates a tomographic image (also referred to as "B mode image") of the inside of the subject.

For example, tomographic image generating section 3 temporally continuously accumulates, in a line memory, signal intensities of an ultrasonic echo detected after ultrasonic probe 200 transmits a pulsed ultrasound beam in the depth direction. In addition, along with scanning of the inside of the subject by using the ultrasound beam from ultrasonic probe 200, tomographic image generating section 3 successively accumulates the signal intensities of the ultrasonic echo at each scanning position in the line memory, to thereby generate two-dimensional data used as a frame unit. Further, tomographic image generating section 3 generates a tomographic image by converting the signal intensities of the ultrasonic echo detected at each position of the inside of the subject into a brightness value.

PW Doppler image generating section 4 acquires a reception signal from reception section 2 when the PW Doppler mode is executed, detects a Doppler shift frequency generated depending on a blood flow present in a measurement region (also referred to as "sample gate"), and generates a PW Doppler image (see T2 in FIG. 3) based on the Doppler shift frequency.

When ultrasonic probe 200 transmits pulsed ultrasound beams at regular intervals in accordance with a pulse repetition frequency, PW Doppler image generating section 4 samples reception signals related to the ultrasonic echo, in synchronization with the pulse repetition frequency. In addition, for example, PW Doppler image generating section 4 detects a Doppler shift frequency based on a calculated phase difference between an ultrasonic echo related to an n-th ultrasound beam and an ultrasonic echo related to an n+1-th ultrasound beam from the same depth position by an FFT analysis. Further, PW Doppler image generating section 4 generates a PW Doppler image by calculating a blood flow velocity from the Doppler shift frequency.

Note that, the blood flow velocity is calculated by using equation 1 below based on a Doppler shift frequency of an ultrasonic echo and on a crossing angle (see θ in FIG. 3) between a beam direction (see the arrow in FIG. 3) of the ultrasound beam and an extending direction of a blood vessel (the same applies to color Doppler image generating section 5 and power Doppler image generating section 6).

$$V = c/2 \cos\theta \times Fd/F0 \quad \text{(Equation 1)}$$

(where V: blood flow velocity, F0: transmission frequency (or reception frequency) of an ultrasound beam, Fd: Doppler shift frequency, c: in vivo sound velocity, and θ: angle correction value (a crossing angle between a beam direction of an ultrasound beam and an extending direction of a blood vessel)).

For example, as illustrated in T2 in FIG. 3, the PW Doppler image is an image representing a time series distribution of a blood flow velocity in a measurement region where the time is represented by the horizontal axis and the blood flow velocity is represented by the vertical axis. In the PW Doppler image, for example, the blood flow velocity at each time point is represented in a single line-like form, and power of each blood flow velocity (that is, each frequency) is represented by a magnitude of brightness of a pixel (illustration of changes in brightness is omitted in FIG. 3).

Color Doppler image generating section 5 acquires a reception signal from reception section 2 when the color Doppler mode is executed, detects a Doppler shift frequency generated depending on a blood flow present in a measurement region, and generates a color Doppler image (see T3 in FIG. 3) based on the Doppler shift frequency.

Color Doppler image generating section 5 acquires, for example, ultrasonic echoes, reflected from positions at the same depth, of continuously transmitted pulsed ultrasound beams. Color Doppler image generating section 5 then detects Doppler shift frequencies of the ultrasonic echoes by an analysis based on autocorrelation processing. Thereafter, color Doppler image generating section 5 generates a color Doppler image by expressing, by a color space vector, the velocity, power, and velocity turbulence of the blood flow or the like, which are converted from the Doppler shift frequencies of the ultrasound echoes.

Note that, color Doppler image generating section 5 detects Doppler shift frequencies of ultrasonic echoes at each position of a measurement region (also referred to as "region of interest (ROI)") set by control device 10 (Doppler parameter setting section 12), and calculates a blood flow velocity or the like. At this time, an ultrasound beam is transmitted so as to scan the inside of the subject along the scanning direction of the measurement region, for example, and, for ultrasonic echoes at each scanning position, color Doppler image generating section 5 detects Doppler shift frequencies at each depth position of the measurement region. Thus, color Doppler image generating section 5 maps blood flow information in a two-dimensional shape and generates a color Doppler image.

Power Doppler image generating section 6 acquires a reception signal from reception section 2 when the power Doppler mode is executed, detects a Doppler shift frequency generated depending on a blood flow present in a measurement region, and generates a power Doppler image (not illustrated) based on the Doppler shift frequency.

Power Doppler image generating section 6 generates a quadrature detection signal (that is, an IQ signal) indicating a Doppler shift frequency by quadrature detection processing, for example. Power Doppler image generating section 6 then calculates power of the blood flow in the measurement region by performing power operation of the quadrature detection signal, and generates a power Doppler image by expressing the power by a color space vector.

Note that, as in the color Doppler mode, power Doppler image generating section 6 detects Doppler shift frequencies of ultrasonic echoes at each position of a measurement region set by control device 10 (Doppler parameter setting section 12) and generates a power Doppler image in which blood flow information is mapped in a two-dimensional shape.

Note that, the "Doppler image generating section" of the present invention corresponds to one of PW Doppler image generating section 4, color Doppler image generating section 5 and power Doppler image generating section 6, or to a generic term thereof.

Display processing section 7 acquires a tomographic image output from tomographic image generating section 3, a PW Doppler image output from PW Doppler image generating section 4, a color Doppler image output from color Doppler image generating section 5 or a power Doppler image output from power Doppler image generating section 6, and generates a display image to be displayed on monitor 8. For example, in a case where a color Doppler image or a power Doppler image is generated, display processing section 7 performs image synthesis so as to superimpose the color Doppler image or the power Doppler image on a measurement region of the color Doppler image or the power Doppler image in the tomographic image, to thereby generate a display image (see T1 and T3 in FIG. 3).

Note that, when display processing section 7 generates a display image, display processing section 7 may use a tomographic image and a Doppler image that are subjected to coordinate transformation processing, data interpolation processing, gamma correction processing or the like.

Further, display processing section 7 generates a display image in which a user interface image (hereinafter, referred to as "execution mode selection UI image") for allowing a user to select which of the B mode, the PW Doppler mode, the color Doppler mode, and the power Doppler mode is executed is embedded, for example (see T4 in FIG. 3).

Further, when the Doppler mode (the PW Doppler mode, the Color Doppler mode, or the Power Doppler mode) is executed, for example, display processing section 7 generates a display image in which a user interface image (hereinafter, referred to as "measurement parameter setting UI image") for allowing a user to change settings of a measurement region, a region size, and a steering angle of an ultrasound beam in the Doppler mode is embedded (see T5 in FIG. 3).

Note that, in ultrasound diagnostic apparatus A according to the present embodiment, a measurement region or the like in the Doppler mode is configured to be automatically set such that the measurement region is set at a position where a blood vessel in a tomographic image is clearly projected. Accordingly, in a case when a user commands a measurement region or the like to be changed in the measurement parameter setting UI image, a position for which the change command is performed is set as a specified position, and a measurement region is set at a position near the specified position and where a blood vessel is clearly projected (details will be described later).

The monitor screen of FIG. 3 is an example of a display image generated by display processing section 7. "Tall" in FIG. 3 represents the entire region of the displayed image, T1 represents a tomographic image (T1X is a blood flow region, and T1Y is a tissue region), T2 represents a PW Doppler image, T3 represents a color Doppler image, T4 represents the execution mode selection UI image, and T5 represents the measurement parameter setting UI image.

In FIG. 3, execution mode selection UI image T4 is formed by UI image T4a that receives a command to execute the B mode, UI image T4b that receives a command to execute the PW Doppler mode, UI image T4c that receives a command to execute the color Doppler mode, and UI image T4d that receives a command to execute the power Doppler mode. This embodiment is configured such that a user is capable of switching the imaging mode to be executed by selecting one of UI images T4a to T4d described above.

Further, in FIG. 3, measurement parameter setting UI image T5 is formed by UI image T5a that receives a setting change of a position of a measurement region, UI image T5b that receives a setting change of the region size of a measurement region, and UI image T5c that receives a setting change of a steering angle of an ultrasound beam. This embodiment is configured such that a user selects UI images T5a to T5c described above, and thereby a UI image for a setting change of a measurement region or the like is displayed.

Note that, T5aa of FIG. 3 indicates an example of an UI image for changing settings of a measurement region displayed when UI image T5a is selected. For example, UI image T5aa is configured to be displayed so as to move in tomographic image T1 in accordance with a mouse operation of a user and is configured such that the user is capable of setting, while viewing tomographic image T1 and UI image T5aa, a specified position in tomographic image T1.

Note that, tomographic image generating section 3, PW Doppler image generating section 4, color Doppler image generating section 5, power Doppler image generating section 6, and display processing section 7 are implemented as, for example, a digital operation circuit formed by a digital signal processor (DSP) or the like. However, these configurations are variously deformable and, for example, some or all thereof may be implemented as a dedicated hardware circuit or may be implemented by operation processing in accordance with a program.

Monitor 8 (corresponding to "display section" of the present invention) is a display that displays a display image generated by display processing section 7, and is, for example, configured as a liquid crystal display.

Operation input section 9 is a user interface for a user to perform an input operation and is formed by, for example, a mouse, a push-button switch, a keyboard, and/or the like. Operation input section 9 converts an input operation performed by a user into an operation signal and inputs the operation signal into control device 10.

Control device 10 transmits and receives signals to and from ultrasonic probe 200, transmission section 1, reception section 2, tomographic image generating section 3, PW Doppler image generating section 4, color Doppler image generating section 5, power Doppler image generating section 6, display processing section 7, monitor 8, and operation input section 9, and integrally controls these sections. Note that, control device 10 includes, for example, a central processing unit (CPU), a read-only memory (ROM), a random access memory (RAM), and the like. In addition, each function of control device 10 is implemented by the CPU referring to a control program and various types of data stored in the ROM or the RAM. However, some or all of the functions of control device 10 are not necessarily implemented by processing by software, and can of course also be implemented by a dedicated hardware circuit or a combination thereof.

Control device 10 includes transmission-reception control section 11 and Doppler parameter setting section 12.

Transmission-reception control section 11 controls the channel switching section (not illustrated) of ultrasonic probe 200 to selectively determine driving target channels among the plurality of channels. Further, transmission-reception control section 11 controls each of transmission section 1 and reception section 2 to transmit and receive ultrasound for the driving target channels.

Here, when the B mode is executed (that is, when a tomographic image is generated), transmission-reception control section 11 sequentially drives the driving target channels among the plurality of channels along the scanning direction, thereby causing ultrasonic probe 200 to scan the inside of the subject with ultrasound.

Further, when the PW Doppler mode, the color Doppler mode or the power Doppler mode is executed, transmission-reception control section 11 selectively drives the plurality of transducers provided in ultrasonic probe 200 such that an ultrasound beam is transmitted from ultrasonic probe 200 to a measurement region in the subject.

Transmission-reception control section 11 basically determines transmission and reception conditions of an ultrasound beam based on e.g. the type of ultrasonic probe 200 (for example, convex type, sector type, linear type or the like), the depth of an imaging target in the subject, and the imaging mode (for example, B mode, PW Doppler mode, color Doppler mode, or power Doppler mode), which are set by a user via operation input section 9.

When the PW Doppler mode, the color Doppler mode, or the power Doppler mode is executed, however, transmission-reception control section 11 determines the transmission and reception conditions of an ultrasound beam based on a measurement region, the size of the measurement region, and a steering angle of the ultrasound beam, which are set by Doppler parameter setting section 12.

When the PW Doppler mode, the color Doppler mode or the power Doppler mode is executed, Doppler parameter setting section 12 automatically sets the measurement region, the size of the measurement region, and the steering angle of the ultrasound beam in the imaging modes described above, based on image information on a tomographic image. Note that, hereinafter, these measurement conditions are also referred to as "measurement region or the like in the Doppler mode".

Here, Doppler parameter setting section 12 according to the present embodiment is configured such that a measurement region or the like in the Doppler mode can be specified by an operation of a user (for example, measurement parameter setting UI image T5 in FIG. 3). However, in a case where a measurement region in the Doppler mode is specified by an operation of a user, the specified position may deviate from a preferred position for blood flow measurement (that is, a position where a blood vessel is clearly projected). Alternatively, the preferred position for blood flow measurement may temporally change due to movement of the subject or movement of ultrasonic probe 200 during ultrasonography.

From such a viewpoint, by setting a search condition according to a specified position specified by a user when a position of a blood vessel is detected from a tomographic image, Doppler parameter setting section 12 according to the present embodiment is configured to be capable of automatically setting a measurement region or the like in the Doppler mode, while meeting the user's intention and at a position where a blood flow can be measured in the subject (details will be described later).

[Detailed Configuration of Doppler Parameter Setting Section]

Next, a detailed configuration of Doppler parameter setting section 12 will be described with reference to FIGS. 4 to 10.

Figure 4:
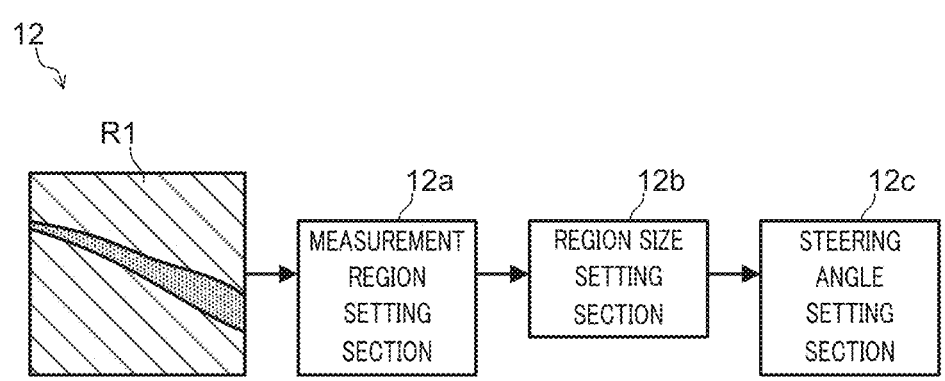
FIG. 4 is a diagram illustrating a detailed configuration of a Doppler parameter setting section according to the embodiment.

FIG. 4 is a diagram illustrating a detailed configuration of Doppler parameter setting section 12 according to the present embodiment.

Doppler parameter setting section 12 includes measurement region setting section 12a, region size setting section 12b, and steering angle setting section 12c.

<Measurement Region Setting Section 12a>

Measurement region setting section 12a acquires tomographic image R1 generated by tomographic image generating section 3, searches for a position of a blood vessel of the subject from tomographic image R1 described above, and sets the position of the blood vessel detected in the tomographic image as the measurement region described above. For example, measurement region setting section 12a uses data of blood vessel patterns (that is, template images) recorded in a memory (not illustrated) in advance and detects a position of a blood vessel projected in tomographic image R1 by publicly-known template matching. Note that, the measurement region set by measurement region setting section 12a is, for example, a measurement range in which blood flow information is acquired in the Doppler mode.

However, in a case where a measurement region has been already set or in a case where a specified position specified by a user exists when measurement region setting section 12a automatically sets a measurement region, measurement region setting section 12a sets a search condition for when searching for a position of a blood vessel in tomographic image R1 such that the measurement region is automatically set near the measurement region that has been already set or near the specified position. Further, in a case where no measurement region is set in advance and a specified position specified by a user does not exist when measurement region setting section 12a automatically sets a measurement region, measurement region setting section 12a sets a search condition for when searching for a position of a blood vessel in tomographic image R1 such that the measurement region is automatically set near a center of tomographic image R1.

Here, the "specified position" is a position in tomographic image R1, which is input by a user via operation input section 9 as a position of an examination target for blood flow information. The "specified position" is represented by, for example, two-dimensional coordinates in tomographic image R1. For example, a user sets the "specified position" by moving, while visually recognizing tomographic image R1 displayed on monitor 8, a UI image for specifying a measurement region (for example, UI image T5aa), which is displayed on monitor 8, to a desired position in tomographic image R1 by using operation input section 9 (for example, a mouse). Note that, the "specified position" may be a specified region having a certain range.

Figure 14:
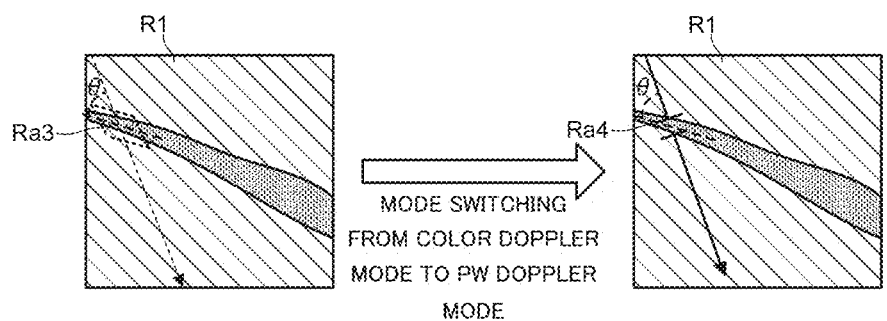

Further, examples of the "case where a measurement region has been already set" include a case where resetting of a measurement region is triggered by an operation of a user, switching of the imaging mode, or the like (see FIG. 14 or the like).

Further, the "search condition" here is a condition for regulating in tomographic image R1a region in which a position of a blood vessel is detected. Examples of the "search condition" include weights set for each position of tomographic image R1 when a position of a blood vessel is searched for in tomographic image R1, a search range when a position of a blood vessel is searched for in tomographic image R1, and the like.

FIGS. 5A and 5B are diagrams illustrating examples of weights set by measurement region setting section 12a for each position of tomographic image R1 as a search condition. FIG. 5A is a diagram illustrating an example of weights set for each position of tomographic image R1 in a case where a specified position specified by a user does not exist. FIG. 5B is a diagram illustrating an example of weights set for each position of tomographic image R1 in a case where a specified position specified by a user (here, a specified position is set near an upper left portion of tomographic image R1) exists.

In a case where measurement region setting section 12a sets weights as a search condition, measurement region setting section 12a integrates weights set for each position in tomographic image R1 with respect to similarities calculated at the each position during template matching, for example, to thereby correct the similarities calculated at the each position. That is, measurement region setting section 12a operates so as to selectively increase, among the similarities calculated at the each position, a similarity calculated at a position with a large weight. During template matching, measurement region setting section 12a selects, as a position of a blood vessel to be measured, a position with the highest similarity to a template image. Accordingly, the above-described weighting processing results in a state in which a blood vessel present at a position to which a large weight is given is more likely to be determined as a measurement region than a blood vessel present at a position to which a small weight is given.

At this time, in a case where a specified position does not exist, the largest weight value is given to region Rs1a near the center of tomographic image R1 and smaller weight values are stepwise given from the center of tomographic image R1 outward as illustrated in FIG. 5A, for example. In a case where a specified position exists, on the other hand, the largest weight value is given to region Rs2a near the specified position of tomographic image R1 (here, a position near the upper left portion of tomographic image R1) and smaller weight values are stepwise given as the distance from the specified position of tomographic image R1 increases as illustrated in FIG. 5B, for example.

Figure 6:
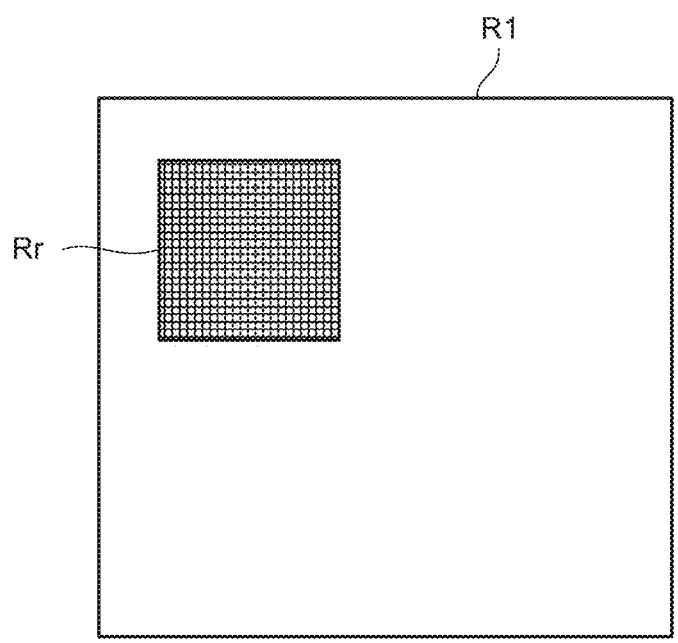
FIG. 6 is a diagram illustrating an example of a search range set by the measurement region setting section according to the embodiment as a search condition.

FIG. 6 is a diagram illustrating an example of a search range set by measurement region setting section 12a as a search condition. FIG. 6 indicates a form in which only region Rr near a specified position is set as a search range when a position of a blood vessel is searched for in tomographic image R1.

In a case where measurement region setting section 12a sets as a search condition a search range when a position of a blood vessel is searched for in tomographic image R1, measurement region setting section 12a operates so as to detect a blood vessel only from within the search range.

Figure 7:
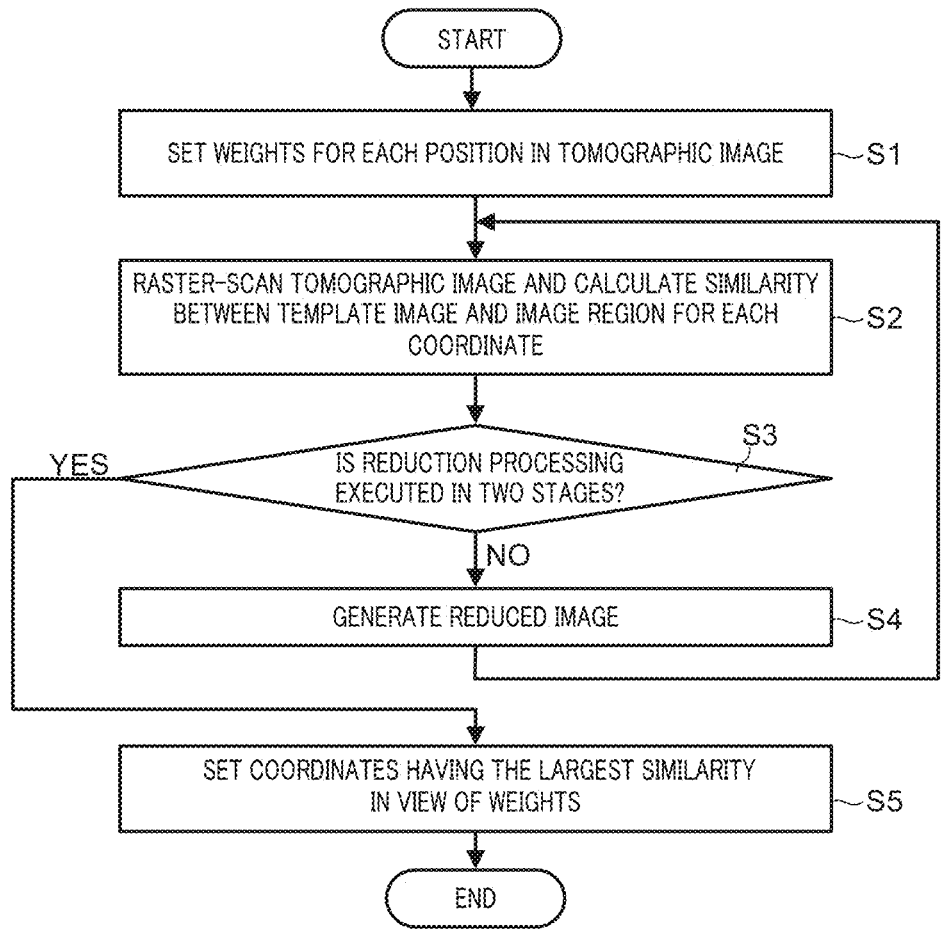
FIG. 7 is a diagram illustrating an example of processing by the measurement region setting section according to the embodiment.
Figure 8:
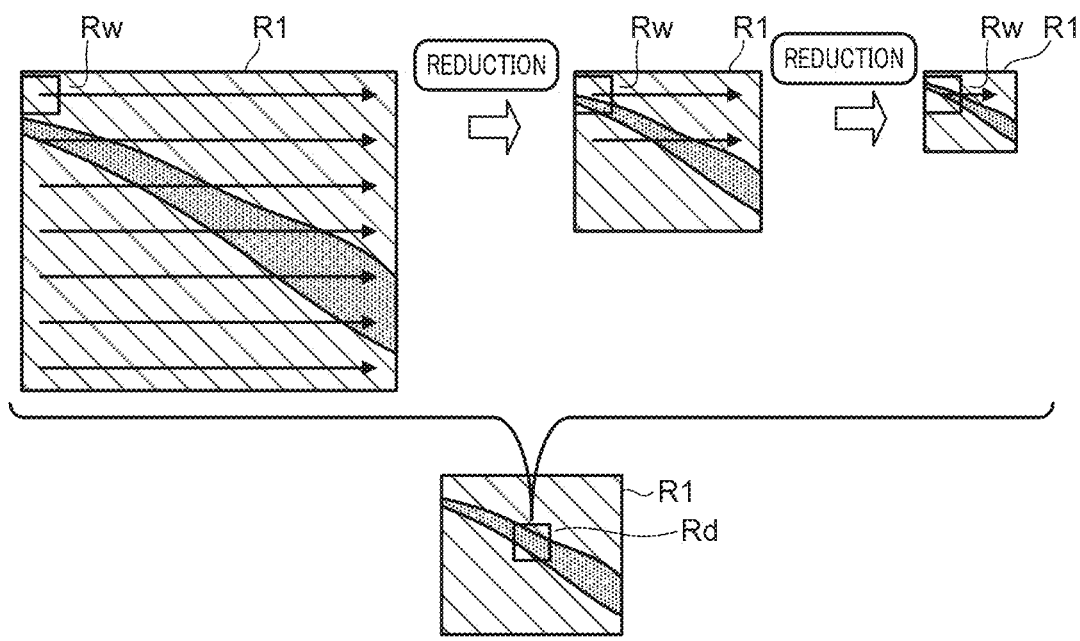
FIG. 8 is a diagram illustrating the example of the processing by the measurement region setting section according to the embodiment.

FIGS. 7 and 8 are diagrams illustrating an example of processing by measurement region setting section 12a according to the present embodiment.

First, in step S1, measurement region setting section 12a sets weights for each position in tomographic image R1 based on a specified position.

Next, in step S2, measurement region setting section 12a reads out a template image of a blood vessel. Then, measurement region setting section 12a sequentially sets comparison target image regions (hereinafter, referred to as "comparison target regions") having the same size (for example, 100 pixels×100 pixels) as template image Rw in tomographic image R1 so as to raster-scan an inside of tomographic image R1, for example, and calculates similarities to template image Rw for each of the comparison target regions. Thereafter, measurement region setting section 12a calculates similarities to template image Rw for each coordinate in tomographic image R1. Thus, measurement region setting section 12a searches for a region where a blood vessel is clearly projected in tomographic image R1.

Next, in step S3, measurement region setting section 12a determines whether or not reduction processing in subsequent step S4 is executed in two stages. In addition, in a case where the reduction processing in step S4 is executed in two stages (step S3: YES), the processing proceeds to step S5. In a case where the reduction processing of step S4 is not executed in two stages (step S3: NO), the processing proceeds to step S4.

Next, in step S4, measurement region setting section 12a generates a reduced image by reducing tomographic image R1 by a predetermined magnification (for example, 0.9 times). Then, measurement region setting section 12a returns to step S2, and performs template matching for the reduced image by using the template image of the blood vessel in a similar fashion, and calculates similarities for each coordinate of the reduced image. In this case, the same template as the template of the blood vessel applied to original tomographic image R1 is used without changing the size of the template image of the blood vessel. Note that, this search processing using a reduced image is processing in which a case where the size of a blood vessel is different from that of a template image is taken into consideration.

Next, in step S5, measurement region setting section 12a selects coordinates with the largest similarity from each coordinate of tomographic image R1, each coordinate of the reduced image, and each coordinate of the re-reduced image (tomographic image R1 subjected to two-step reduction) in view of weights set for each position in tomographic image R1.

Note that, in step S5, measurement region setting section 12a integrates the weights set for each position calculated in steps S2 to S4 with respect to the similarities of the each position, for example, to thereby correct the similarities calculated at the each position. Then, measurement region setting section 12a selects coordinates with the largest similarity based on the corrected similarities of each position.

As described above, in a case where a specified position specified by a user exists when a measurement region in the Doppler mode is automatically set, measurement region setting section 12a executes template matching such that the measurement region is automatically set near the specified position. Thus, it is possible to set a measurement region at a position which a user wishes as an examination target for blood flow information in tomographic image R1, and where a blood vessel is clearly projected in tomographic image R1.

Note that, the reason why measurement region setting section 12a is configured such that a measurement region is automatically set near the center of tomographic image R1 in a case where no measurement region is set in advance and a specified position specified by a user does not exist is that tomographic image R1 is generally captured such that a position of a blood vessel that a user wishes to view comes near the center of tomographic image R1 described above. Accordingly, when switching from a state in which the B mode is executed to the Doppler mode or the like is performed (that is, when a specified position specified by a user does not exist), for example, it can be said that setting a measurement region near the center of tomographic image R1 meets the user's intention.

Data related to a "specified position" is also used, for example, when the imaging mode is switched or when a measurement region is reset (description will be given later with reference to FIGS. 11 to 13), and is therefore preferably retained once set. However, specified position information that is recorded in data related to a "specified position" may be replaced, once a measurement region is automatically set near the specified position by an operation of measurement region setting section 12a, with the measurement region.

On the other hand, data related to a "specified position" is preferably resetted in a case where the subject is changed or in a case where an imaging target portion of the subject is changed. The reason is that in a case where examination is shifted to a subject different from a current subject or the subject is the same but the imaging target portion is shifted to a portion different from a current portion during ultrasonography, it can be said that returning to a status at the time of initial settings meets the intention of a user. Note that, a change of the subject can be recognized, for example, by a subject ID set in ultrasound diagnostic apparatus A. Further, a change of the imaging target portion may be recognized, for example, by imaging target portion information set in ultrasound diagnostic apparatus A or by a sensor signal of a gyroscopic sensor (not illustrated) built in ultrasonic probe 200. Further, data related to a "specified position" may also be reset when a state in which the PW Doppler mode, the color Doppler mode, or the power Doppler mode is executed is changed to a state in which the B mode is executed.

<Region Size Setting Section 12b>

Region size setting section 12b detects boundary positions (that is, wall parts of a blood vessel) between the blood vessel and an extravascular tissue in a region around coordinates set by measurement region setting section 12a as a measurement region in tomographic image R1. Then, region size setting section 12b sets, based on the boundary positions, the size of a measurement region when the Doppler mode is executed.

Figure 9:
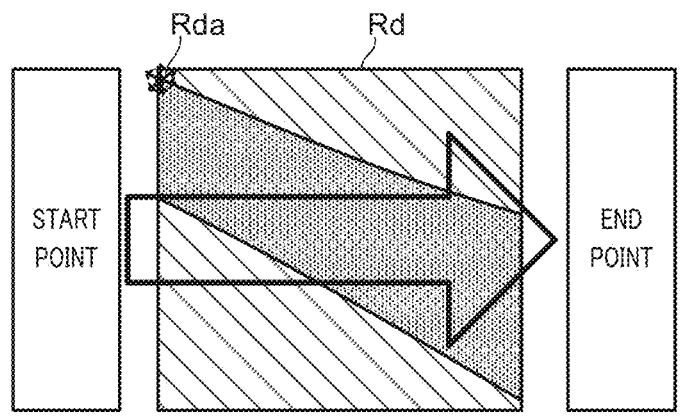
FIG. 9 is a diagram schematically illustrating processing executed by a region size setting section according to the embodiment.

FIG. 9 is a diagram schematically illustrating processing executed by region size setting section 12b according to the present embodiment.

In image region Rd around coordinates set as a measurement region in tomographic image R1, for example, region size setting section 12b performs path search by regarding a path, in which edges are strong and are smoothly continuous, as a boundary between a blood vessel and an extravascular tissue. Specifically, region size setting section 12b replaces a problem of boundary detection with a problem of path search in which a path whose cost is a minimum is searched for, and searches for a path whose cost is a minimum, from a side of a left end of image region Rd (Rda in FIG. 9). In this case, a direction in which edges are small and a direction in which a path is not smooth are each regarded as directions in which cost becomes larger.

Thus, region size setting section 12b detects a boundary position between an upper-side wall part of a blood vessel and an extravascular tissue and a boundary position between a lower-side wall part of the blood vessel and the extravascular tissue. Region size setting section 12b then sets a width between the boundary position of the boundary position of the upper-side wall part of the blood vessel and the boundary position of the lower-side wall part of the blood vessel as a region size.

Here, the size of a measurement region set by region size setting section 12b is a size in the depth direction.

The size of a measurement region is expressed as, for example, a size in the depth direction centered on a measurement region set by measurement region setting section 12a. Note that, in the color Doppler mode or the power Doppler mode, the range of a measurement region (region of interest) having a two-dimensional shape is set based on a size in the depth direction set by region size setting section 12b and a size in a predetermined scanning direction, for example. Further, in the PW Doppler mode, the width of a range gate is set by the size of the measurement region described above.

<Steering Angle Setting Section 12c>

Steering angle setting section 12c detects an extending direction of a blood vessel in a measurement region set by measurement region setting section 12a, based on boundary positions of a blood vessel detected by region size setting section 12b. Then, based on the extending direction of the blood vessel in the measurement region, steering angle setting section 12c sets a steering angle of an ultrasound beam when the Doppler mode is executed.

Figure 10:
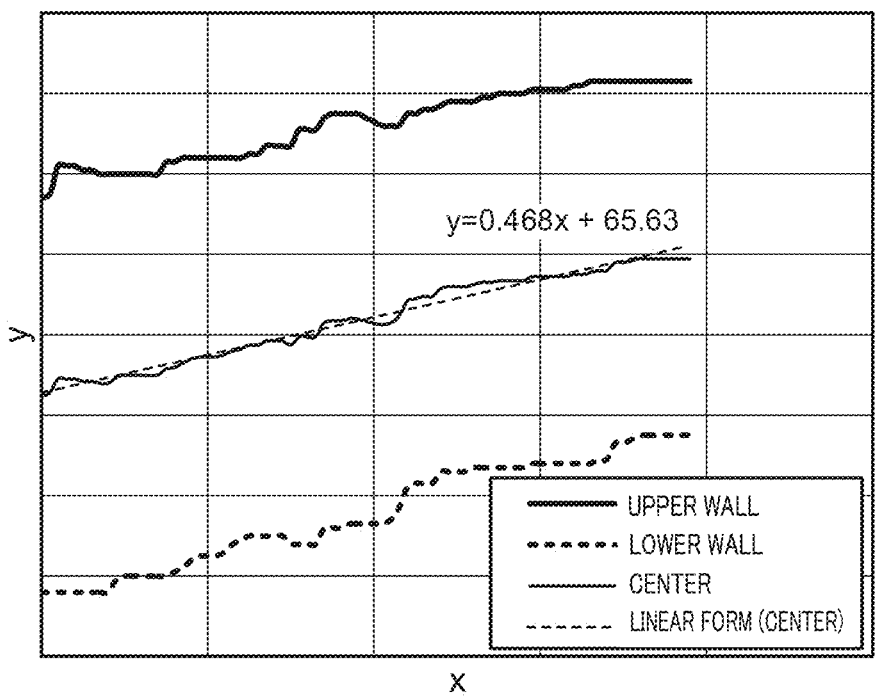
FIG. 10 is a diagram schematically illustrating processing executed by a steering angle setting section according to the embodiment.
Figure 11:
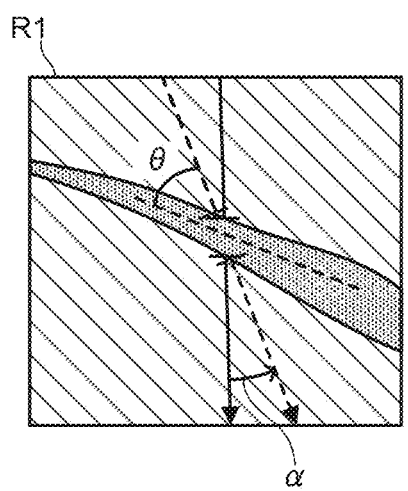
FIG. 11 is a diagram schematically illustrating the processing executed by the steering angle setting section according to the embodiment.

FIGS. 10 and 11 are diagrams schematically illustrating processing executed by steering angle setting section 12c according to the present embodiment.

For example, steering angle setting section 12c calculates an average value of an extending direction of a boundary of an upper-side wall part of a blood vessel and an extending direction of a boundary of a lower-side wall part of the blood vessel based on boundary positions of a blood vessel detected by region size setting section 12b, and specifies the average value as the extending direction of the blood vessel. Note that, in FIG. 10, the extending direction of the blood vessel is calculated as an inclination angle in an XY coordinate system where the scanning direction in tomographic image R1 is the X-axis and the depth direction therein is the Y-axis.

Steering angle setting section 12c then sets a steering angle (angle α in FIG. 11) of an ultrasound beam such that a crossing angle (angle θ in FIG. 11) between a beam direction of an ultrasound beam and an extending direction of a blood vessel in a measurement region is maximally reduced, for example. This is because the smaller the crossing angle between the beam direction of the ultrasound beam and the blood flow direction is, the easier it is to detect a Doppler shift frequency from an ultrasonic echo.

Note that, in a case where an extending direction of a blood vessel at a position of the blood vessel is a direction orthogonal to an image surface of a tomographic image, steering angle setting section 12c sets a steering angle of an ultrasound beam to the zero degree.

After determining a steering angle, steering angle setting section 12c sets the angle correction value of equation 1 described above in order to calculate a blood flow velocity from a Doppler shift frequency. The angle correction value is usually set to the same value as a crossing angle between a beam direction of an ultrasound beam and a blood flow direction, which is determined by setting a steering angle of an ultrasound beam. However, in a case where a crossing angle between a beam direction of an ultrasound beam and a blood flow direction exceeds a threshold angle (for example, 60 degrees), steering angle setting section 12c may set, in view of a significant increase in error in the blood flow velocity due to an error between an actual value and a set value of the crossing angle, the above-described threshold angle (for example, 60 degrees) as the angle correction value rather than the actual crossing angle.

<Operation of Doppler Parameter Setting Section 12>

Next, an example of operation of Doppler parameter setting section 12 will be described with reference to FIGS. 12 to 15.

Doppler parameter setting section 12 causes measurement region setting section 12a, region size setting section 12b, and steering angle setting section 12c described above to automatically set the measurement region, the region size, and the steering angle when the Doppler mode is executed, at predetermined timings.

Figure 12:
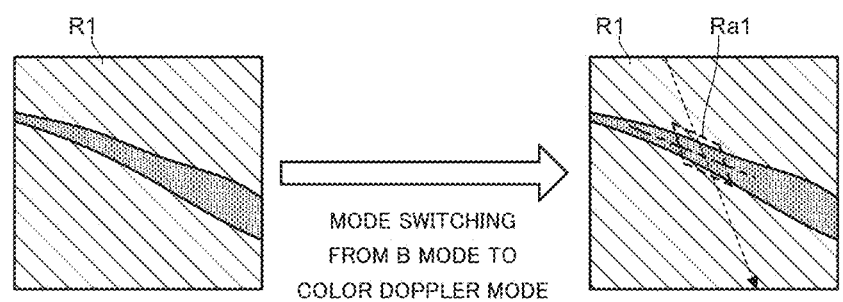
Figure 13:
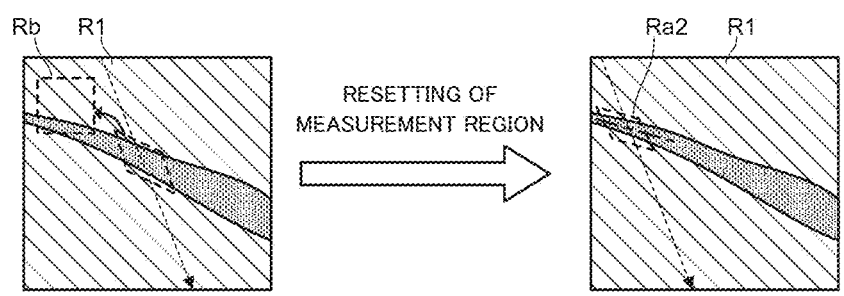

FIGS. 12, 13 and 14 are diagrams illustrating examples of timings at which Doppler parameter setting section 12 according to the present embodiment executes processing of automatically setting a measurement region or the like.

Specifically, examples of the timings at which Doppler parameter setting section 12 executes the processing of automatically setting a measurement region or the like in the Doppler mode include: (1) a timing at which an imaging mode executed in ultrasound diagnostic apparatus A is switched from the B mode to the color Doppler mode, the power Doppler mode, or the PW Doppler mode (see FIG. 12), (2) a timing at which an imaging mode executed in ultrasound diagnostic apparatus A is switched from one imaging mode of the color Doppler mode, the power Doppler mode, or the PW Doppler mode to another imaging mode of the color Doppler mode, the power Doppler mode, or the PW Doppler mode (see FIG. 13), (3) a timing at which a setting change of a measurement region is received from a user when one imaging mode of the color Doppler mode, the power Doppler mode, or the PW Doppler mode is executed in ultrasound diagnostic apparatus A (see FIG. 14), (4) a timing at which a predetermined time has elapsed after an automatic setting of a measurement region or the like in the Doppler mode when one imaging mode of the color Doppler mode, the power Doppler mode, or the PW Doppler mode is executed, and the like.

As in FIG. 12, when an imaging mode executed at a current point is the B mode, a specified position specified by a user usually does not exist. Accordingly, when the B mode is switched to the color Doppler mode thereafter, Doppler parameter setting section 12 sets a search condition such that a measurement region is set near the center of tomographic image R1, searches for a position of a blood vessel, and sets the measurement region or the like based on the search result. Note that, Ra1 represents a measurement region of the color Doppler mode (that is, a measurement region) set by automatic setting processing.

On the other hand, as in FIG. 13, in a case where a command to change a setting of a measurement region is performed by a user and a specified position is set when the color Doppler mode is executed, Doppler parameter setting section 12 sets a measurement region or the like by setting a search condition such that the measurement region is set near the specified position in tomographic image R1. Note that, Rb represents a position specified when a command to change a setting of a measurement region is performed by a user, and Ra2 represents a measurement region of the color Doppler mode (that is, a measurement region) set by automatic setting processing.

On the other hand, as in FIG. 14, in a case where a measurement region (that is, a specified position) is set at an upper left position of tomographic image R1 by a user when the color Doppler mode is executed, Doppler parameter setting section 12 sets a measurement region or the like, when the color Doppler mode is switched to the PW Doppler mode thereafter, by setting a search condition such that a measurement region of the PW Doppler mode is set near the measurement region when the color Doppler mode is executed. Note that, Ra3 represents a measurement region when the color Doppler mode is executed, and Ra4 represents a measurement region of the PW Doppler mode set by automatic setting processing.

Figure 15:
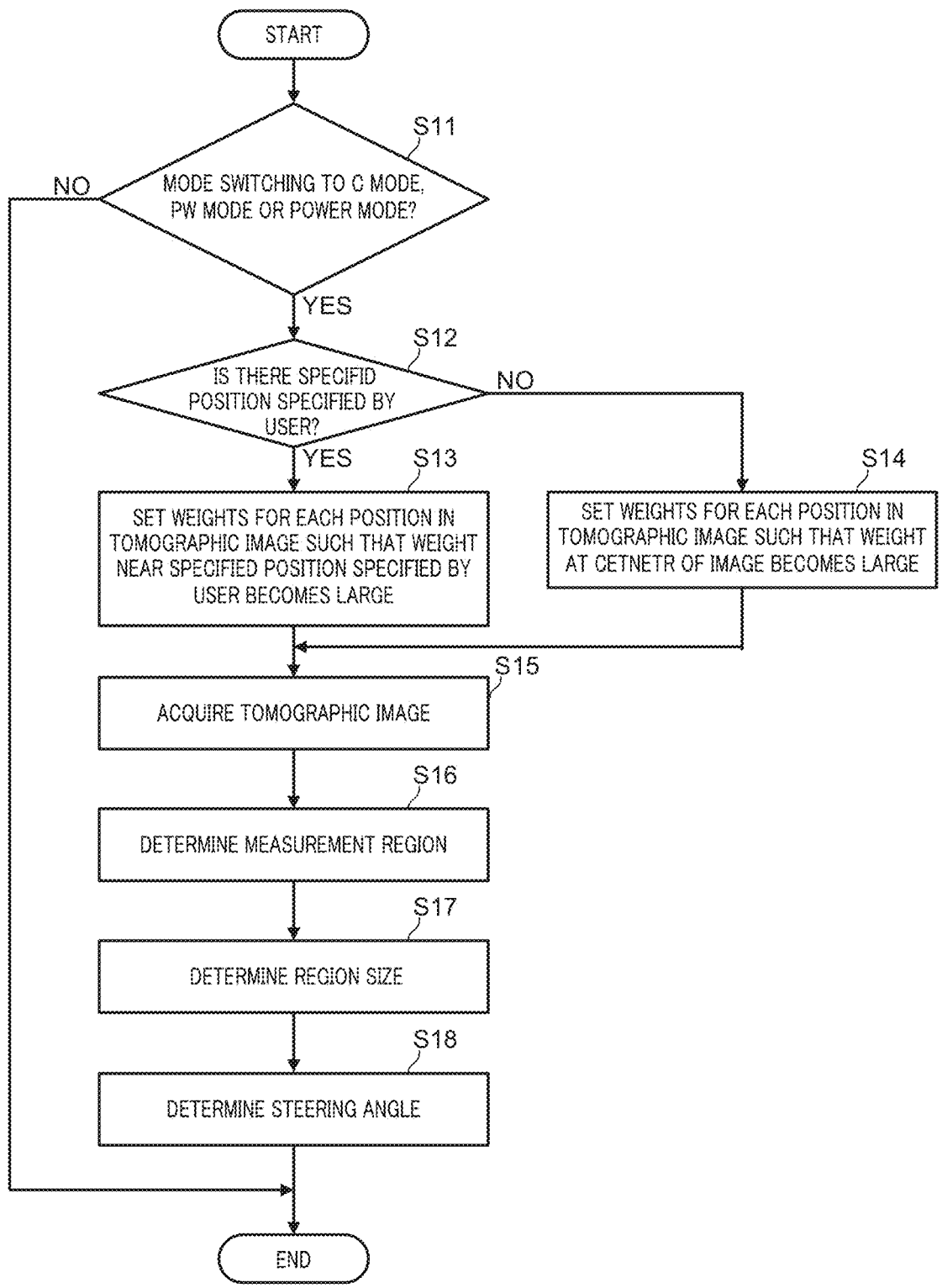
FIG. 15 is a flowchart illustrating an example of operation of the Doppler parameter setting section according to the embodiment.

FIG. 15 is a flowchart illustrating an example of operation of Doppler parameter setting section 12 according to the present embodiment. The flowchart illustrated in FIG. 15 indicates, for example, processing repeatedly executed by Doppler parameter setting section 12 at predetermined intervals (for example, 100-ms intervals) in accordance with a computer program. Note that, the flowchart illustrated in FIG. 15 indicates a form in which a measurement region is automatically set at a timing at which the imaging mode is switched.

In step S11, Doppler parameter setting section 12 first determines whether or not there is a command to switch the mode to one of the PW Doppler mode, the color Doppler mode, and the power Doppler mode by an operation of a user. In a case where the mode switching is executed (S11: YES), Doppler parameter setting section 12 advances the processing to step S12. In a case where the mode switching is not executed (S11: NO), Doppler parameter setting section 12 terminates the processing of the flowchart of FIG. 15.

In step S12, Doppler parameter setting section 12 determines whether or not a specified position specified by the user is retained in a storage section (for example, the RAM of control device 10). Then, in a case where the position specified by the user is retained in the storage section (S12:

YES), Doppler parameter setting section 12 advances the processing to step S13, and in a case where the specified position specified by the user is not retained in the storage section (S12: NO), Doppler parameter setting section 12 advances the processing to step S14.

In step S13, Doppler parameter setting section 12 sets weights for each position in a tomographic image such that a weight near the specified position specified by the user becomes large.

In step S14, Doppler parameter setting section 12 sets weights for each position in the tomographic image such that a weight at a position of a center of the tomographic image becomes large.

In step S15, Doppler parameter setting section 12 acquires the tomographic image.

In step S16, Doppler parameter setting section 12 searches for a position of a blood vessel from the tomographic image by template matching, for example, and determines a measurement region in view of the weights set in step S13 or S14 (see the flowchart of FIG. 7).

In step S17, Doppler parameter setting section 12 detects boundary positions of the blood vessel at the position of the blood vessel determined as the measurement region, and determines the size of the measurement region.

In step S18, Doppler parameter setting section 12 detects an extending direction of the blood vessel at the position of the blood vessel determined as the measurement region, and determines a steering angle of an ultrasound beam based on the extending direction of the blood vessel. At this time, Doppler parameter setting section 12 determines the steering angle of the ultrasound beam such that a crossing angle between the extending direction of the blood vessel and the beam direction of the ultrasound beam is maximally reduced. Then, Doppler parameter setting section 12 sets the crossing angle between the extending direction of the blood vessel and the beam direction of the ultrasound beam when the steering angle of the ultrasound beam is determined, as an angle correction value used in calculating a blood flow velocity. In a case where the crossing angle exceeds a threshold angle (for example, 60 degrees), however, Doppler parameter setting section 12 sets the angle correction value to be the threshold angle.

Through a series of processing as described above, Doppler parameter setting section 12 automatically sets a measurement region or the like when the Doppler mode is executed.

Effects

As described above, in a case where a measurement region has been already set or in a case where a specified position specified by a user exists when ultrasound diagnostic apparatus A (Doppler parameter setting section 12) according to the present embodiment automatically sets a measurement region in the Doppler mode, ultrasound diagnostic apparatus A sets a search condition (for example, weights or a search range) such that the measurement region is automatically set near the measurement region that has been already set or near the specified position, and then executes processing of searching for a position of a blood vessel.

Thus, it is possible to automatically set a measurement region in the Doppler mode, while meeting the intention of a user, and at a position where a blood flow can be measured in a subject. Thus, it is possible to reduce an operation load for a user when setting a measurement region in the Doppler mode.

Further, in particular in a case where an imaging mode executed in ultrasound diagnostic apparatus A (Doppler parameter setting section 12) according to the present embodiment is switched from one imaging mode of the color Doppler mode, the power Doppler mode, or the PW Doppler mode to another imaging mode of the color Doppler mode, the power Doppler mode, or the PW Doppler mode, ultrasound diagnostic apparatus A uses a measurement region set in an imaging mode at a current point or a position specified by an operation of a user when the measurement region is set, as a specified position, and executes processing of automatically setting the measurement region.

Generally, switching from one imaging mode of the color Doppler mode, the power Doppler mode, or the PW Doppler mode to another imaging mode of the color Doppler mode, the power Doppler mode, or the PW Doppler mode is performed when a user wishes to confirm blood flow information related to the same vessel position in another Doppler mode. In this regard, the above-described configuration of ultrasound diagnostic apparatus A (Doppler parameter setting section 12) according to the present embodiment makes it possible to automatically set, even when the imaging mode is switched, a measurement region in the Doppler mode, while meeting the intention of a user, and at a position where a blood flow can be measured in a subject.

Further, in particular in a case where a specified position does not exist when ultrasound diagnostic apparatus A (Doppler parameter setting section 12) according to the present embodiment automatically sets a measurement region in the Doppler mode, ultrasound diagnostic apparatus A sets a search condition such that the measurement region is automatically set near a center of a tomographic image.

Thus, even when e.g. a tomographic image of a new subject is captured, it is possible to automatically set a measurement region in the Doppler mode, while meeting the intention of a user, and at a position where a blood flow can be measured in a subject.

Other Embodiments

The present invention is not limited to the embodiment described above, and various modified forms are possible.

The embodiment described above has indicated, as an example of Doppler parameter setting section 12, a form in which the search condition when a position of a blood vessel is detected is the same even in a case where any imaging mode of the PW Doppler mode, the color Doppler mode, and the power Doppler mode is executed. However, Doppler parameter setting section 12 may change the search condition when a position of a blood vessel is detected, in accordance with the imaging mode to be executed.

Further, the embodiment described above has indicated, as an example of Doppler parameter setting section 12, a form in which every function of measurement region setting section 12a, region size setting section 12b, and steering angle setting section 12c is implemented in a case where a measurement region when the Doppler mode is executed is set. However, Doppler parameter setting section 12 may implement only the function of measurement region setting section 12a in a case where a measurement region when the Doppler mode is executed is set. In this case, for the region size and the steering angle, Doppler parameter setting section 12 may retain the currently set region size and steering angle as they are. On the other hand, in a case where a measurement region when the Doppler mode is executed is set, Doppler parameter setting section 12 may implement only the functions of measurement region setting section 12a and region size setting section 12b or may implement only the functions of measurement region setting section 12a and steering angle setting section 12c.

Further, the embodiment described above has indicated, as examples to which Doppler parameter setting section 12 is applied, the B mode, the PW Doppler mode, the color Doppler mode, and the power Doppler mode. However, the configuration of Doppler parameter setting section 12 is also applicable when ultrasound diagnostic apparatus A operates in the CW Doppler mode.

Further, the embodiment described above has indicated template matching as an example of a technique of causing Doppler parameter setting section 12 to search for a position of a blood vessel. However, the technique of pattern matching when Doppler parameter setting section 12 searches for a position of a blood vessel may be arbitrary. For example, a discriminator (for example, a CNN) that already completes learning by machine learning may be used.

Although embodiments of the present invention have been described and illustrated in detail, the disclosed embodiments are made for purpose of illustration and example only and not limitation. The scope of the present invention should be interpreted by terms of the appended claims.

INDUSTRIAL APPLICABILITY

According to the ultrasound diagnostic apparatus according to the present disclosure, it is possible to reduce, while reflecting the intention of a user, an operation load for a user when setting a measurement region in the Doppler mode.

What is claimed is:

1. An ultrasound diagnostic apparatus, comprising:
a hardware processor that:
generates a tomographic image of an inside of a subject based on a reception signal related to an ultrasonic echo of a first ultrasound beam transmitted so as to scan the inside of the subject;
performs a search for a position of a blood vessel of the subject in the tomographic image and automatically sets a region corresponding to the position of the blood vessel detected in the tomographic image as a measurement region, the search including calculating similarities of a plurality of positions in the tomographic image to a template of a blood vessel pattern; and
generates a Doppler image based on a reception signal related to an ultrasonic echo of a second ultrasound beam transmitted to the measurement region,
wherein in a case where a specified position of a measurement region has been previously set or is specified by a user when the hardware processor automatically sets the measurement region, the hardware processor sets a search condition and executes processing of searching for the position of the blood vessel, wherein the search condition includes weights set for each position of the tomographic image when the position of the blood vessel is searched for in the tomographic image, with largest weight values of the weights given in an area of the specified position and with smaller weight values of the weights stepwise given as the distance from the specified position increases, and the weights are applied to the search results of the search such that, among the similarities calculated at the plurality of positions in the tomographic image, a similarity calculated at a position with a large weight is increased, whereby the measurement region is more likely to be automatically set near the specified position.

2. The ultrasound diagnostic apparatus according to claim 1, wherein
the hardware processor receives a setting change of the measurement region by an operation of the user, and when receiving the setting change, the hardware processor uses a position specified by the operation of the user as the specified position and executes processing of automatically setting the measurement region.

3. The ultrasound diagnostic apparatus according to claim 1, wherein
the hardware processor executes processing of automatically setting the measurement region when execution of one imaging mode of a color Doppler mode, a power Doppler mode, or a Pulse Width (PW) Doppler mode is started in the ultrasound diagnostic apparatus.

4. The ultrasound diagnostic apparatus according to claim 3, wherein:
the hardware processor executes the processing of automatically setting the measurement region when execution of the color Doppler mode or the power Doppler mode is started in the ultrasound diagnostic apparatus, wherein the measurement region is a region of interest.

5. The ultrasound diagnostic apparatus according to claim 3, wherein:
the hardware processor executes the processing of automatically setting the measurement region when execution of the PW Doppler mode is started in the ultrasound diagnostic apparatus, wherein the measurement region is a sample gate in the PW Doppler mode.

6. The ultrasound diagnostic apparatus according to claim 4, wherein
in a case where an imaging mode executed by the ultrasound diagnostic apparatus is switched from one imaging mode of the color Doppler mode, the power Doppler mode, or the PW Doppler mode to another imaging mode of the color Doppler mode, the power Doppler mode, or the PW Doppler mode, the hardware processor uses the measurement region set in an imaging mode at a current point or a position specified by an operation of the user when the measurement region is set, as the specified position, and executes the processing of automatically setting the measurement region.

7. The ultrasound diagnostic apparatus according to claim 1, wherein
in a case where no measurement region is set in advance and the specified position does not exist when the hardware processor automatically sets the measurement region, the hardware processor automatically sets the measurement region near a center of the tomographic image and executes the processing of searching for the position of the blood vessel.

8. The ultrasound diagnostic apparatus according to claim 7, wherein
the hardware processor resets data related to the specified position in a case where the subject is changed or in a case where an imaging target portion of the subject is changed.

9. The ultrasound diagnostic apparatus according to claim 1, wherein
the hardware processor detects an extending direction of the blood vessel at the position of the blood vessel set as the measurement region, based on image information on the tomographic image, and automatically sets a steering angle of the second ultrasound beam based on the extending direction of the blood vessel.

10. The ultrasound diagnostic apparatus according to claim 9, wherein the steering angle is set such that a crossing angle between a beam direction of the second ultrasound beam and the extending direction of the blood vessel does not exceed a threshold angle, the crossing angle being determined in accordance with the steering angle.

11. The ultrasound diagnostic apparatus according to claim 1, wherein in a case where a crossing angle between a beam direction of the second ultrasound beam and an extending direction of the blood vessel exceeds a threshold angle, the hardware processor sets an angle correction value related to the crossing angle as the threshold angle, the angle correction value being referred to when a blood flow velocity is calculated from a Doppler shift frequency.

12. The ultrasound diagnostic apparatus according to claim 11, wherein in a case where the crossing angle is equal to or less than the threshold angle, the hardware processor sets the angle correction value to be the crossing angle.

13. The ultrasound diagnostic apparatus according to claim 1, further comprising a display that displays an image in which an image indicating the measurement region is superimposed on the tomographic image.

14. The ultrasound diagnostic apparatus according to claim 1, wherein the hardware processor further displays a user interface image for setting the specified position by the operation of the user.

15. A method of controlling an ultrasound diagnostic apparatus, comprising:

generating a tomographic image of an inside of a subject based on a reception signal related to an ultrasonic echo of a first ultrasound beam transmitted so as to scan the inside of the subject;

searching for a position of a blood vessel of the subject in the tomographic image, and automatically setting a region corresponding to the position of the blood vessel detected in the tomographic image as a measurement region, the searching including calculating similarities of a plurality of positions in the tomographic image to a template of a blood vessel pattern; and generating a Doppler image based on a reception signal related to an ultrasonic echo of a second ultrasound beam transmitted to the measurement region, wherein in a case where a specified position of a measurement region has been previously set or is specified by a user when the measurement region is automatically set, setting a search condition and searching for the position of the blood vessel, wherein the search condition includes weights set for each position of the tomographic image when the position of the blood vessel is searched for in the tomographic image, with largest weight values of the weights given in an area of the specified position and with smaller weight values of the weights stepwise given as the distance from the specified position increases, and the weights are applied to the search results of the search such that, among the similarities calculated at the plurality of positions in the tomographic image, a similarity calculated at a position with a large weight is increased, whereby the measurement region is more likely to be automatically set near the specified position.

16. A non-transitory computer-readable recording medium storing therein a computer readable program for controlling an ultrasound diagnostic apparatus, the program causing a computer to perform:

generating a tomographic image of an inside of a subject based on a reception signal related to an ultrasonic echo of a first ultrasound beam transmitted so as to scan the inside of the subject;

searching for a position of a blood vessel of the subject in the tomographic image, and automatically setting a region corresponding to the position of the blood vessel detected in the tomographic image as a measurement region, the searching including calculating similarities of a plurality of positions in the tomographic image to a template of a blood vessel pattern; and generating a Doppler image based on a reception signal related to an ultrasonic echo of a second ultrasound beam transmitted to the measurement region, in a case where a specified position of a measurement region has been previously set or is specified by the user when the measurement region is automatically set, setting a search condition and searching for the position of the blood vessel, wherein the search condition includes weights set for each position of the tomographic image when the position of the blood vessel is searched for in the tomographic image, with largest weight values of the weights given in an area of the specified position and with smaller weight values of the weights stepwise given as the distance from the specified position increases, and the weights are applied to the search results of the search such that, among the similarities calculated at the plurality of positions in the tomographic image, a similarity calculated at a position with a large weight is increased, whereby the measurement region is more likely to be automatically set near the specified position.

17. The ultrasound diagnostic apparatus according to claim 1, wherein calculating similarities using the template is performed on the tomographic image and on a reduced size of the tomographic image.

18. The ultrasound diagnostic apparatus according to claim 1, wherein in a case where a specified position of a measurement region has not been previously set and is not specified by a user when the hardware processor automatically sets the measurement region, the largest weight values of the weights are given to a center of the tomographic image with smaller weight values of the weights stepwise given as the distance from the center increases.

* * * * *